US011504515B2

(12) United States Patent
Calias et al.

(10) Patent No.: US 11,504,515 B2
(45) Date of Patent: Nov. 22, 2022

(54) ACCESS PORT SYSTEM WITH SELF-ADJUSTING CATHETER LENGTH

(71) Applicant: IMOTIK BIOSOLUTIONS LLC, Acton, MA (US)

(72) Inventors: Pericles Calias, Melrose, MA (US); Michel Morency, Boxborough, MA (US)

(73) Assignee: IMOTIK BIOSOLUTIONS LLC, Acton, MA (US)

( * ) Notice: Subject to any disclaimer, the term of this patent is extended or adjusted under 35 U.S.C. 154(b) by 0 days.

(21) Appl. No.: 16/769,134

(22) PCT Filed: Nov. 14, 2019

(86) PCT No.: PCT/US2019/061454
§ 371 (c)(1),
(2) Date: Jun. 2, 2020

(87) PCT Pub. No.: WO2020/102516
PCT Pub. Date: May 22, 2020

(65) Prior Publication Data
US 2021/0146108 A1  May 20, 2021

Related U.S. Application Data

(60) Provisional application No. 62/767,927, filed on Nov. 15, 2018.

(51) Int. Cl.
*A61M 39/02* (2006.01)
*A61M 39/04* (2006.01)

(52) U.S. Cl.
CPC ........ *A61M 39/0208* (2013.01); *A61M 39/04* (2013.01)

(58) Field of Classification Search
CPC .............. A61M 39/0208; A61M 39/04; A61M 25/0113; A61M 2039/0235;
(Continued)

(56) References Cited

U.S. PATENT DOCUMENTS 3,253,594 A * 5/1966 Matthews ......... A61M 39/0247
604/178
3,461,869 A * 8/1969 Hargest ............. A61M 39/0247
623/66.1
(Continued)

OTHER PUBLICATIONS

Albrecht et al., "Intraparenchymal Migration of an Intrathecal Catheter Three Years After Implantation", Pain, vol. 118, 2005, pp. 274-278.
(Continued)

*Primary Examiner* — Theodore J Stigell
(74) *Attorney, Agent, or Firm* — Adler Pollock & Sheehan P.C.; Michel Morency

(57) ABSTRACT

Described herein is an implantable access port device with a catheter compartment which permits lengthening or shortening the catheter in response to changes in tension of the distal catheter. Implantable access port devices are used extensively in the medical field to facilitate the performance of recurrent therapeutic tasks such as repeated drug delivery, drainage, blood sampling, transfusions, or total parental nutrition. In current access port systems, the catheter is rigidly attached to the access port via a connection ring. As such, the system does not provide any flexibility or ability for catheter length adjustments, which can lead to long-term complications such as dislodgement of catheters, migration of catheters, port separation with extravasation, suture disruption, and mechanical failure of the access port system. These catheter-related complications carry serious risks for the patients. The implantable access port system described (Continued)

herein permits self-adjusting catheter length, thereby reducing catheter-related complications.

14 Claims, 9 Drawing Sheets

(58) Field of Classification Search
CPC .. A61M 2039/0258; A61M 2039/0232; A61M 2039/0273; A61M 2039/0261; A61M 39/08; A61M 2039/0223
See application file for complete search history.

(56) References Cited

U.S. PATENT DOCUMENTS

| | | | | |
|---|---|---|---|---|
| 3,663,965 | A * | 5/1972 | Lee, Jr. | A61M 39/0247 623/23.64 |
| 3,752,162 | A * | 8/1973 | Newash | A61N 1/378 607/113 |
| 4,318,401 | A * | 3/1982 | Zimmerman | A61M 39/0247 604/165.01 |
| 4,668,222 | A * | 5/1987 | Poirier | A61L 29/041 128/DIG. 26 |
| 4,762,517 | A | 8/1988 | McIntyre et al. | |
| 5,242,415 | A * | 9/1993 | Kantrowitz | A61M 39/0247 604/175 |
| 5,287,852 | A * | 2/1994 | Arkinstall | A61M 16/0465 128/207.14 |
| 5,374,254 | A * | 12/1994 | Burna | A61M 25/02 604/533 |
| 5,662,616 | A * | 9/1997 | Bousquet | A61M 39/0247 128/DIG. 26 |
| 5,713,858 | A * | 2/1998 | Heruth | A61M 39/0247 604/288.02 |
| 7,216,665 | B1 | 5/2007 | Sims, Jr. | |
| 8,152,792 | B1 * | 4/2012 | Kornel | A61M 27/00 604/21 |
| 8,600,479 | B2 | 12/2013 | Dalke et al. | |
| 9,050,446 | B2 | 6/2015 | Marcotte et al. | |
| 9,700,714 | B2 * | 7/2017 | Stem | A61N 1/05 |
| 9,764,124 | B2 * | 9/2017 | Tallarida | A61M 39/22 |
| 10,780,214 | B1 * | 9/2020 | Hensler | A61M 39/1011 |
| 2009/0259187 | A1 * | 10/2009 | Egle | A61M 39/0208 604/174 |
| 2014/0378891 | A1 | 12/2014 | Searle et al. | |
| 2016/0346470 | A1 | 12/2016 | Hayek | |
| 2017/0095654 | A1 * | 4/2017 | Houde | A61M 39/0208 |
| 2017/0182303 | A1 * | 6/2017 | Tallarida | A61M 39/0208 |

OTHER PUBLICATIONS

Anitescu et al., "Intrapleural Migration of a Spinal Catheter in a PatientWith Arachnoiditis and Extensive Epidural Scarring After Tethered Cord Release: A Case Report and Review of Literature", Neuromodulation, 2012, 4 pages.
Aprili et al., "Serious Complications Associated with External Intrathecal Catheters Used in Cancer Pain Patients", A Systematic Review and Meta-analysis, Anesthesiology, vol. 111, No. 6, Dec. 2009, pp. 1346-1355.
Belverud et al., "Intrathecal Pumps", Neurotherapeutics: The Journal of the American Society for Experimental NeuroTherapeutics, vol. 5, Jan. 2008, pp. 114-122.
Follett et al., "A Prospective Study of Catheter-Related Complications of Intrathecal Drug Delivery Systems", Journal of Pain and Symptom Management, vol. 19, No. 3, Mar. 2000, pp. 209-215.
Follett et al., "Prevention of Intrathecal Drug Delivery Catheter-Related Complications", Prevention of Catheter Complications, Neuromodulation, vol. 6, No. 1, 2003, pp. 32-41.
Hayek et al., "Intrathecal Therapy for Cancer and Non-Cancer Pain", Pain Physician, vol. 14, ISSN 1533-3159, 2011, pp. 219-248.
Ho et al., "Dislodgment of Port-A-Cath Catheters in Children", Pediatr Neonatol, vol. 49, Issue 5, 2008, pp. 179-182.
International Search Report and Written Opinion received in International Application No. PCT/US2019/61454, dated Feb. 3, 2020, 11 pages.
Varhabhatla et al., "Rising Complication Rates after Intrathecal Catheter and Pump Placement in the Pediatric Population: Analysis of National Data Between 1997 and 2006", Pain Physician, vol. 15, Jan./Feb. 2012, pp. 65-74.
Hitt et al., Complications of Intrathecal Drug Delivery Systems, Techniques in Regional Anesthesia and Pain Management, vol. 15, 2011, pp. 162-166.

* cited by examiner

ACCESS PORT SYSTEM WITH SELF-ADJUSTING CATHETER LENGTH

CROSS-REFERENCE TO RELATED APPLICATIONS

This present application claims priority as a national stage application submitted under 35 U.S.C. 371 from PCT/US2019/061454 filed Nov. 14, 2019, which claims priority from provisional application number 62/767,927 filed Nov. 15, 2018, the entire contents of each are hereby incorporated by reference herein.

FIELD OF THE INVENTION

The embodiments of the present invention relate to an implantable access port system for the infusion and/or withdrawal of fluids to or from a subject, and particularly an implantable access port system with self-adjusting catheter length.

BACKGROUND OF THE INVENTION

Implantable access port devices are used extensively in the medical field to facilitate the performance of recurrent therapeutic tasks.[1] Treatment of patients often requires long-term vascular or extra-vascular access for safe, repeated drug delivery, drainage, blood sampling, transfusions, or total parental nutrition. Access port systems are also used to access the fluid-filled space around the spinal cord, called the subarachnoid or intrathecal space, for drug delivery and/or sampling of cerebrospinal fluid (CSF).

A typical access port system comprises a needle-impenetrable housing having a fluid reservoir that is sealed by a needle-penetrable septum. The access port also includes an outlet stem or exit cannula which projects from the housing to a connection ring and provides a fluid passageway that communicates with the fluid reservoir. The connection ring is used to couple the housing to a catheter. The access port device is attached to the proximal end of the catheter and the distal end of the catheter is placed into a patient's blood vessel, intrathecal space, other lumen or target tissue. The access port device is generally implanted subcutaneously at a location that is easily accessible.

The catheter is rigidly attached to the access port device via a connection ring. As such, the access port system does not provide any flexibility or ability for catheter length adjustments, which can lead to long-term complications such as dislodgement of catheters, migration of catheters, port separation with extravasation, suture disruption, and mechanical failure of the access port system. These complications carry serious risks for the patients.[2] Although relatively rare in adults for vascular access ports, these complications are significantly more prevalent in pediatric patients.[3]

The rate of complications is significantly higher with implantable intrathecal access port systems as the smaller catheters used in these devices are more susceptible to kinks, breaks, leakage, dislodgement from the intrathecal space, and disconnection from the pump.[4] Catheter-related complications were the most common cause of repeat surgery. The incidence of operative catheter revision has been reported to be 7% to 34.6%.[5] For example, Follet and Naumann[6] reported a 9.7% rate of catheter-related complications in the first nine months after implantation. The most common complication was catheter dislodgement from the intrathecal space. Migration of the catheter completely out of the spinal canal and into the subcutaneous tissues in the paraspinous region is most common. Fluckiger et al. reported the migration of the catheter outside of the dura in approximately 12% of patients.[7] Migration to the subdural compartment or the epidural space has also been reported.

Accordingly, there is a need in the art for improved access port systems which reduce the risk of catheter-related complications.

BRIEF SUMMARY OF THE INVENTION

The present invention is related to various embodiments of an implantable access port system with self-adjusting catheter length. By lengthening or shortening the catheter in response to changes in tension of the distal catheter, use of the implantable access port system of the present disclosure reduces the risk of complications such as dislodgement of catheters, migration of catheters, port separation with extravasation, suture disruption, and mechanical failure of the access port system.

In one embodiment, an access port device has a catheter compartment, wherein a catheter, secured to the access port device, has a portion of a proximal portion of the catheter contained within the catheter compartment and is extensible outside the catheter compartment to increase a length of a distal portion of the catheter or is retractable inside the compartment to decrease the length of the distal portion of the catheter. The catheter compartment can consist of an extension of the access port device with a peripheral wall running along a portion of an exterior edge of a bottom of the access port device. The catheter compartment can also have a base. The catheter compartment can be separate from and secured to the access port device. In one embodiment, the catheter compartment is secured to the access port device with a stretchable biocompatible material in a shape of a sleeve or sock. The above-described access port device can also have a biocompatible flange or skirt extending radially from the access port device in order to provide a greater surface area for suturing the access port device to a patient.

In another embodiment, the implantable access port system of the present invention comprises an access port device having a housing, a septum, a fluid reservoir, a connection ring, and a catheter compartment. In one embodiment, the catheter compartment is located under the housing of the access port and has a peripheral wall and a base. The peripheral wall runs along the exterior edge of the bottom of the access port housing with an opening located under the connection ring of the access port. A catheter, secured to the connection ring, has a portion of the proximal portion of the catheter contained within the catheter compartment and is extensible outside the compartment to increase the length of the distal portion of the catheter or is retractable inside the compartment to decrease the length of the distal portion of the catheter.

In an alternate embodiment, the catheter compartment only has a peripheral wall with opening, but no base. Again, the peripheral wall runs along the exterior edge of the bottom of the access port housing with an opening located under the connection ring of the access port. In this alternate embodiment, once implanted into a patient, the base of the catheter compartment is formed by the patient's subcutaneous tissue. A catheter, secured to the connection ring, has a portion of the proximal portion of the catheter contained within the catheter compartment and is extensible outside the compartment to increase the length of the distal portion of the catheter or is retractable inside the compartment to decrease the length of the distal portion of the catheter.

In yet another alternate embodiment, the exit cannula, connection ring, and catheter exit the base of the access port directly into the catheter compartment instead of exiting the posterior wall of the housing. The catheter compartment has a winder or retractor mechanism, such as a spring-loaded winder, which can take in or release a length of catheter in response to a change in tension of the distal catheter.

The implantable access port device can be sutured to the patient's subcutaneous tissue. In one embodiment, the access port device has suture holes that go through both the housing of the access port and the peripheral wall of the catheter compartment. In an alternate embodiment, the suture holes extend from or go through the peripheral wall of the catheter compartment but not through the housing of the access port. The implantable access port system has 1, 2, 3, 4, 5, 6, 7, 8, 9, 10 or more suture holes. In another alternate embodiment, the access port further comprises a soft, flexible flange or skirt composed of a stretchable, elastic biocompatible material such as rubber, latex, silicone, elastomer (e.g., ChronoPrene™ and other thermoplastic elastomers (TPE), sometimes referred to as thermoplastic rubbers, thermoset elastomers), or other biocompatible material suitable for stitching. This flexible flange or skirt provides significantly greater surface area for securing or stitching the access port device to the patient's subcutaneous tissue.

In one embodiment, the catheter compartment is manufactured as an extension of the access port housing using, for example, injection molding or 3D printer technology. In an alternate embodiment, the catheter compartment is produced separately and secured to the bottom of the access port housing using a securing mean such as, but not limited to, an adhesive, screws, or sutures. In yet another embodiment, the catheter compartment is positioned under the bottom of the access port housing and secured in place by a stretchable biocompatible material in the shape of a sleeve or a sock, with an opening located over the posterior end of the access port system to avoid obstructing the connection ring, the catheter, and the opening of the catheter compartment. The biocompatible sleeve or sock can also have an opening over the septum to provide unimpeded needle penetration. In yet another alternate embodiment, the catheter compartment is built into the biocompatible sleeve or sock, which is then used with a conventional access port available in the art. In some embodiments, the biocompatible sleeve or sock further comprises a flange or skirt composed of a stretchable, elastic biocompatible material such as rubber, latex, silicone, elastomer (e.g., ChronoPrene™ and other thermoplastic elastomers (TPE), thermoset elastomers), or other biocompatible material suitable for stitching. This flexible flange or skirt, which provides additional areas for securing or stitching the access port system to the patient's subcutaneous tissue.

Other implementations are also described and recited herein.

BRIEF DESCRIPTION OF THE DRAWINGS

For the purpose of illustration, certain embodiments of the present invention are shown in the drawings described below. Like numerals in the drawings indicate like elements throughout. It should be understood, however, that the invention is not limited to the precise arrangements, dimensions, and instruments shown. In the drawings.

DETAILED DESCRIPTION OF THE INVENTION

Figure 1A:
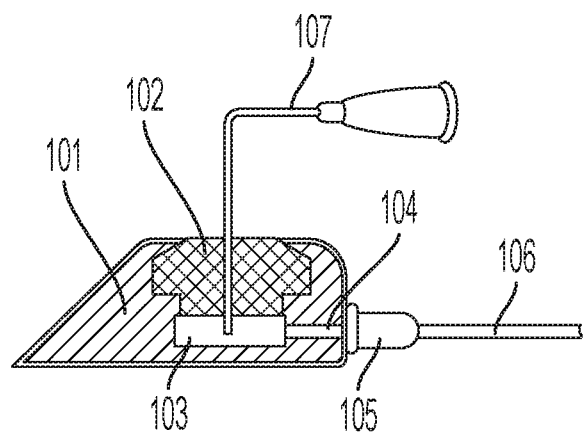
FIG. 1 provides a schematic side cross-sectional view (FIG. 1A), a top perspective view (FIG. 1B), and a bottom perspective view (FIG. 1C) of a typical implantable access port system.

It is to be appreciated that certain aspects, modes, embodiments, variations and features of the invention are described below in various levels of detail in order to provide a substantial understanding of the present invention.

The following description of particular aspect(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the compositions or processes are described as using specific materials or an order of individual steps, it is appreciated that materials or steps may be interchangeable such that the description of the invention may include multiple parts or steps arranged in many ways as is readily appreciated by one of skill in the art.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

As used in this specification and the appended claims, the singular forms "a," "an" and "the" include plural referents unless the content clearly dictates otherwise. For example, reference to "a cell" includes a combination of two or more cells, and the like.

The term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

The term "subject" refers to a mammal, including but not limited to a dog, cat, horse, cow, pig, sheep, goat, chicken, rodent, or primate. Subjects can be house pets (e.g., dogs, cats), agricultural stock animals (e.g., cows, horses, pigs, chickens, etc.), laboratory animals (e.g., mice, rats, rabbits, etc.), but are not so limited. Subjects include human subjects. The human subject may be a pediatric, adult, or a geriatric subject. The human subject may be of either sex. The terms "subject" and "patient" are used interchangeably herein.

The terms "effective amount" and "therapeutically-effective amount" include an amount sufficient to prevent or ameliorate a manifestation of disease or medical condition, such as cancer, an infection, or a genetic disorder. It will be appreciated that there will be many ways known in the art to determine the effective amount for a given application. For example, the pharmacological methods for dosage determination may be used in the therapeutic context. In the context of therapeutic or prophylactic applications, the amount of a composition administered to the subject will depend on the type and severity of the disease and on the characteristics of the subject, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds.

As used herein, the term "biocompatible" means that the components are composed of any substance that has been engineered to be compatible with the body and elicit little or no immunogenicity, carcinogenicity, teratogenicity, and toxicity in a given organism. As such, the biocompatible components are suitable for implantation in a patient.

The terms "treating" or "treatment" or "to treat" or "alleviating" or "to alleviate" refer to both (1) therapeutic measures that cure, slow down, lessen symptoms of, and/or halt progression of a diagnosed disease or infection and (2) prophylactic or preventative measures that prevent or slow the development of a disease or infection.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, the term "long-term" administration means that the therapeutic agent or drug is administered for a period of at least 12 weeks. This includes that the therapeutic agent or drug is administered such that it is effective over, or for, a period of at least 12 weeks and does not necessarily imply that the administration itself takes place for 12 weeks, e.g., if sustained release compositions or long acting therapeutic agent or drug is used. Thus, the subject is treated for a period of at least 12 weeks. In many cases, long-term administration is for at least 4, 5, 6, 7, 8, 9 months or more, or for at least 1, 2, 3, 5, 7 or 10 years, or more.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only and is not intended to limit the scope of the present invention, which is defined solely by the claims.

Other terms are defined herein within the description of the various aspects of the invention.

Medical Uses of Implantable Access Ports

Implantable access ports are used extensively in the medical field to facilitate the performance of recurrent, long-term therapeutic tasks. Treatment of patients (e.g., in oncology, hematology, internal medicine) often requires long-term vascular or extra-vascular access connected to an access port for drug delivery, drainage, blood sampling, transfusions, total parental nutrition.

Figure 1B:
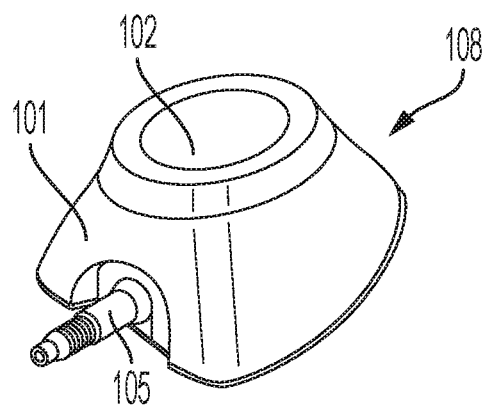
Figure 1C:
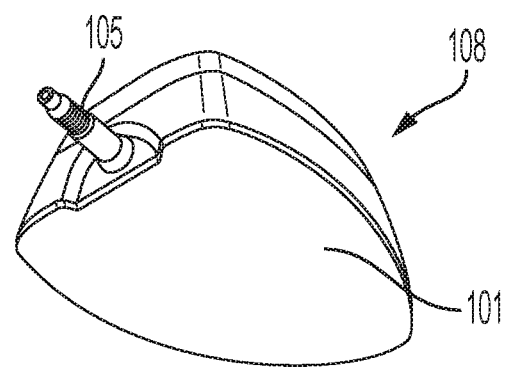

FIG. 1A-C provide schematic, top perspective, and bottom perspective views, respectively, of a typical implantable access port system 108. Access ports typically have a needle-impenetrable housing 101 having a fluid reservoir 103 that is sealed by a needle penetrable septum 102. The access port also includes an exit cannula 104, which projects from the posterior wall of the housing and provides a fluid passageway that communicates with the fluid reservoir. The exit cannula is used to couple the housing to the proximal end of a catheter 106 via a connection ring 105. The distal end of the catheter is placed into a patient's blood vessel, intrathecal space, other lumen or target tissue. The access port is generally implanted subcutaneously at a location that is easily accessible. Fluids can be inserted or withdrawn from the fluid reservoir using a needle 107 via the needle-penetrable septum 102. It may be appreciated that there are many variations to the geometry of the access port. For example, while the housing of the access port in FIG. 1 may be described as a partially pyramidal shape, which can facilitate subcutaneous implantation, the instant disclosure is not so limited.

During the implantation procedure, a subcutaneous pocket is first created to receive and house the access port. This is done by making an incision in the skin of the patient at the intended implantation site for the access port. The access port is then inserted beneath the skin through the incision, with the connection ring of the access port going into the pocket the subcutaneous pocket last. The access port is secured to the patient's subcutaneous tissue usually with one or more sutures. The proximal end of the catheter is then coupled to the connection ring of the access port. The distal end of the catheter is then inserted into the target location (e.g., blood vessel, intrathecal area, other lumen or target tissue).

Once the access port system is implanted, a non-coring needle (e.g., a Huber needle) attached to a feed line may be used to access the implanted access port, by penetrating the septum, to deliver a desired medication. Alternatively, bodily fluids can be withdrawn from the location where the distal end of the catheter is inserted.

Complications with Long-Term Use of Implantable Access Ports

Although implantable vascular access port systems can provide reliable, long-term vascular access for frequent administration of blood products, parenteral nutrition, antibiotics or chemotherapy, serious complications are also associated with their use. These include infection, occlusion, thrombosis, extravasation, migration and dislodgment of the catheter. Although relatively rare, dislodgment carries potentially serious risks of arrhythmia, heart or vessel perforation, cardiac tamponade and even death.[2] The rate of dislodgement has been reported to be higher in children (1.4% to 3.6%)[3] than in adults (0.3% to 1.5%).[8]

The rate of complications is significantly higher with implantable intrathecal access port systems. Catheter-related complications were the most common cause of repeat surgery. The incidence of operative catheter revision has been reported to be 7% to 34.6%.[4] For example, Follet and Naumann[5] reported a 9.7% rate of catheter-related complications in the first nine months after implantation. The most common complication was catheter dislodgement from the intrathecal space. Migration of the catheter completely out of the spinal canal and into the subcutaneous tissues in the paraspinous region is most common. Fluckiger et al. reported the migration of the catheter outside of the dura in approximately 12% of patients.[7] Migration to the subdural compartment or the epidural space has also been reported. Intraparenchymal migration of an intrathecal catheter has also been reported.[9]

Reducing Complications with Improved Access Port Systems

Implantable access ports in the art are rigidly attached to the catheter, which does not provide any flexibility or ability for catheter length adjustments and leads to long-term complications such as dislodgement of catheters, migration of catheters, port separation with extravasation, suture disruption, catheter migration, and mechanical failure of the access port system.

The implantable access port system of the present disclosure reduces the risks of complications by lengthening or shortening the distal catheter in response to changes in tension of the distal catheter. The catheter can be lengthened by having some length of the additional catheter exit the compartment or the catheter can be shortened by having some length of the external catheter enter the compartment. The catheter compartment can either be an integral extension of the housing of a conventional access port or a separate component that is secured to a conventional access port.

Figure 2A:
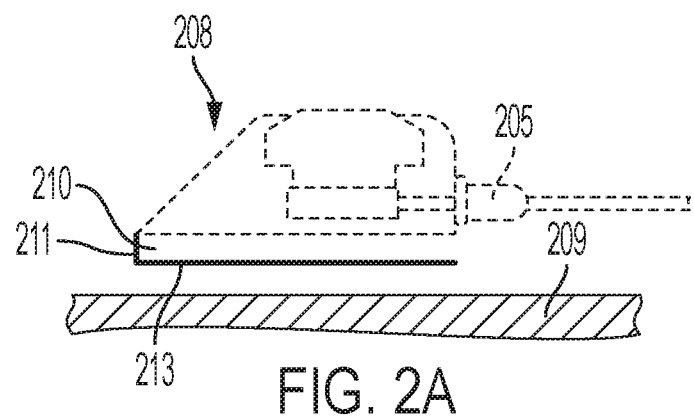
FIG. 2 provides a schematic side cross-sectional view (FIG. 2A), a top perspective view (FIG. 2B), and a bottom perspective view (FIG. 2C) of the access port system (shown in dotted and dashed lines) with a catheter compartment having a peripheral wall and a base.
Figure 2B:
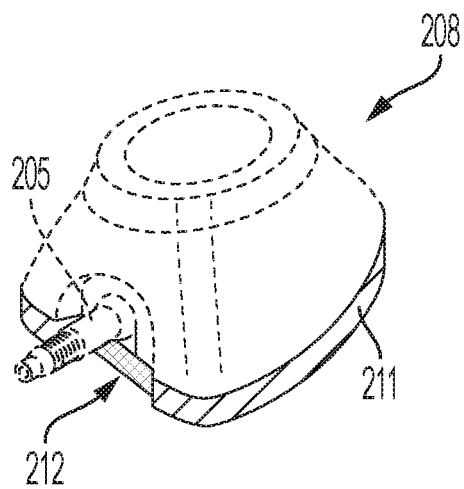
Figure 2C:
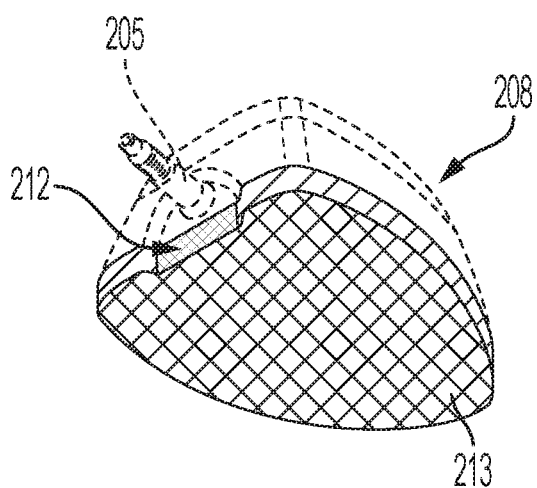

For a catheter compartment that is an extension of the housing of a conventional access port, the catheter compartment can have a lateral wall, a base, and an opening. FIG. 2 provide schematic cross-sectional side perspective (FIG. 2A), top perspective (FIG. 2B), and bottom perspective (FIG. 2C) views of a typical implantable access port system 208 (shown in dotted and dashed lines) with a catheter compartment comprising a peripheral wall 211 and a base 213, the peripheral wall 211 extending along almost the entire circumference of the lower part of the access port with an opening 212 located under the connection ring 205. During the surgical procedure, the access port system 208 and catheter compartment 210 are implanted subcutaneously and secured to the patient subcutaneous tissue 209.

Figure 3A:
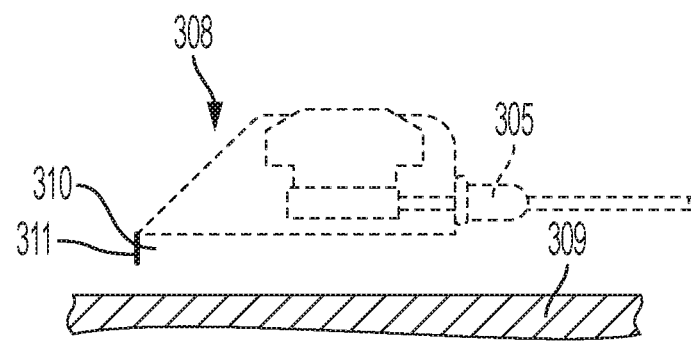
FIG. 3 provides a schematic side cross-sectional view (FIG. 3A), a top perspective view (FIG. 3B), and a bottom perspective view (FIG. 3C) of the access port system (shown in dotted and dashed lines) with a catheter compartment having only a peripheral wall.
Figure 3B:
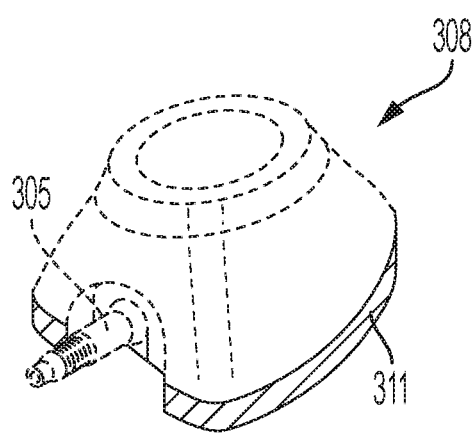
Figure 3C:
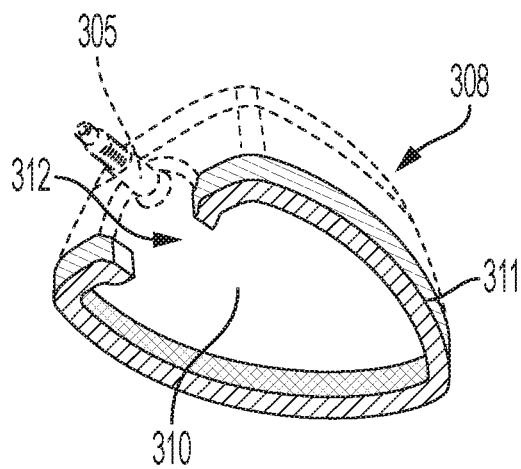

In an alternative embodiment, the catheter compartment extending from the housing does not have a base; it only has a lateral wall extending along almost the entire circumference of the lower part of the access port. FIG. 3 provide schematic cross-sectional side perspective (FIG. 3A), top perspective (FIG. 3B), and bottom perspective (FIG. 3C) views of a typical implantable access port system 308 (shown in dotted and dashed lines) with a catheter compartment 310 having only a peripheral wall 311 extending along almost the entire circumference of the lower part of the access port with an opening 312 under the connection ring 305. During the surgical procedure, the access port system 308 is implanted subcutaneously with the peripheral wall 311 resting on and secured to the patient's subcutaneous tissue 309. The catheter compartment is thus formed by the bottom portion of the access port, the peripheral wall 311, with the patient's subcutaneous tissue 309 forming the base. In this embodiment, the one or more loops of the catheter can only be inserted in the catheter compartment 310 after the access port device has been secured to the patient's subcutaneous tissue.

Figure 4A:
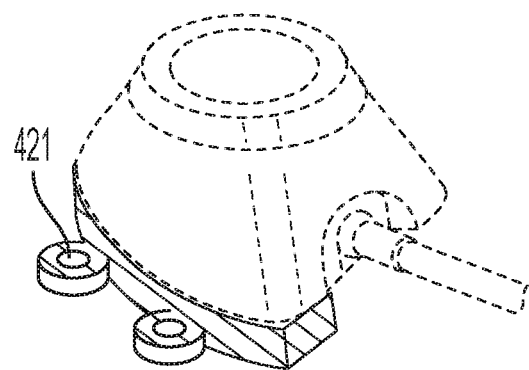
FIG. 4 illustrates an access port system with suture holes extending from the catheter chamber peripheral wall (FIG. 4A, top perspective view); an access port system with suture holes embedded into the housing and catheter chamber peripheral wall (FIG. 4B, top perspective view); and an access port system with a biocompatible flange or skirt extending radially from the housing (FIG. 4C-D, top and bottom perspective view, respectively).
Figure 4B:
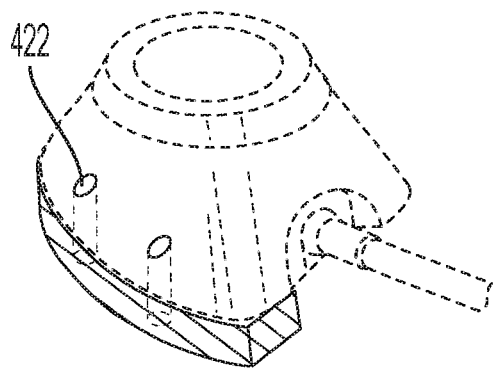
Figure 4C:
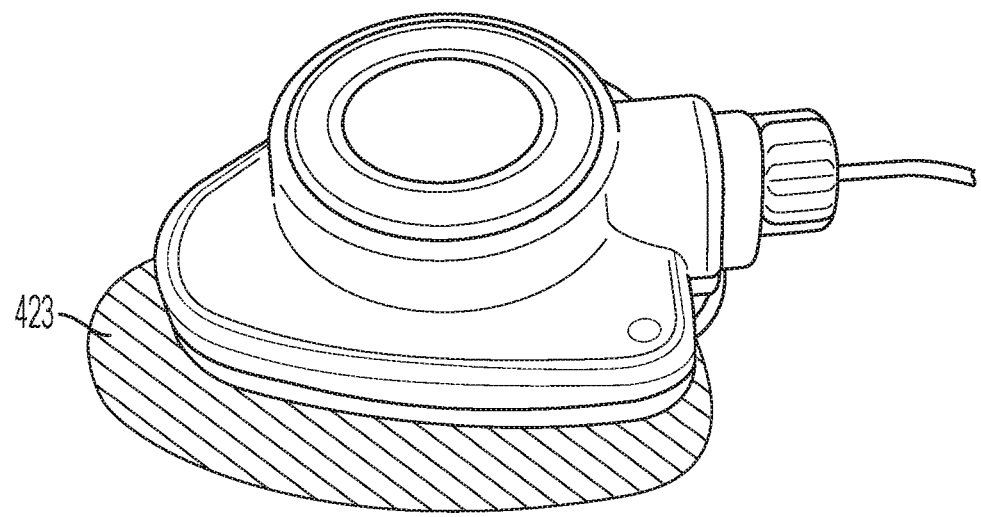
Figure 4D:
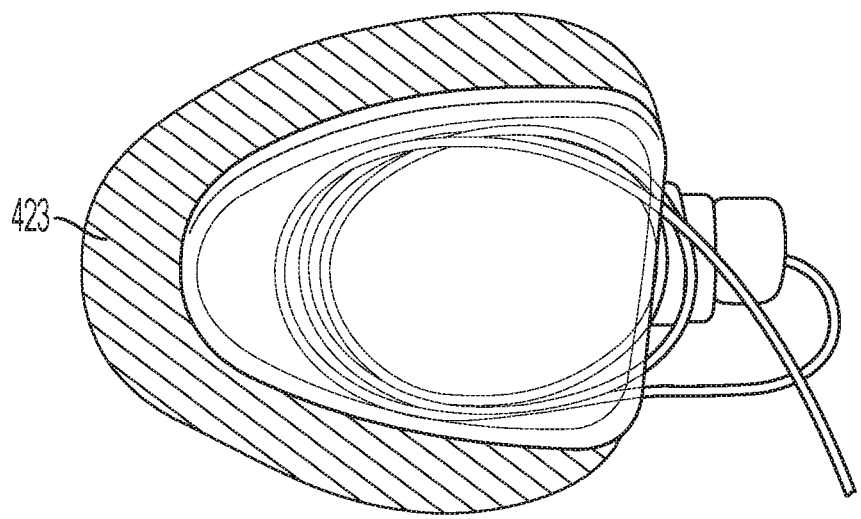

Once the access port system has been implanted subcutaneously, it is secured to the patient's subcutaneous tissue 209 or 309 with, for example, sutures through suture holes extending from peripheral wall (421 in FIG. 4A) or both the access port housing and the peripheral wall (422 in FIG. 4B). An access port system can have 1, 2, 3, 4, 5, 6, 7, 8, or more suture holes. In an alternate embodiment, the access port system has a biocompatible flange or skirt extending radially from the peripheral wall of the housing (423 in FIG. 4C-D), which is composed of a stretchable, elastic biocompatible material such as rubber, latex, silicone, elastomer (e.g., ChronoPrene™ and other thermoplastic elastomers (TPE), thermoset elastomers), or other suitable biocompatible material. The flange or skirt provides a much greater surface area for securing or stitching the access port system to the patient's subcutaneous tissue. It does not have to run along the edge of the entire circumference of the access port device. In an alternative embodiment, the access port device can have 1, 2, 3 or more partial flange or skirts around the circumference of the device.

Figure 5:
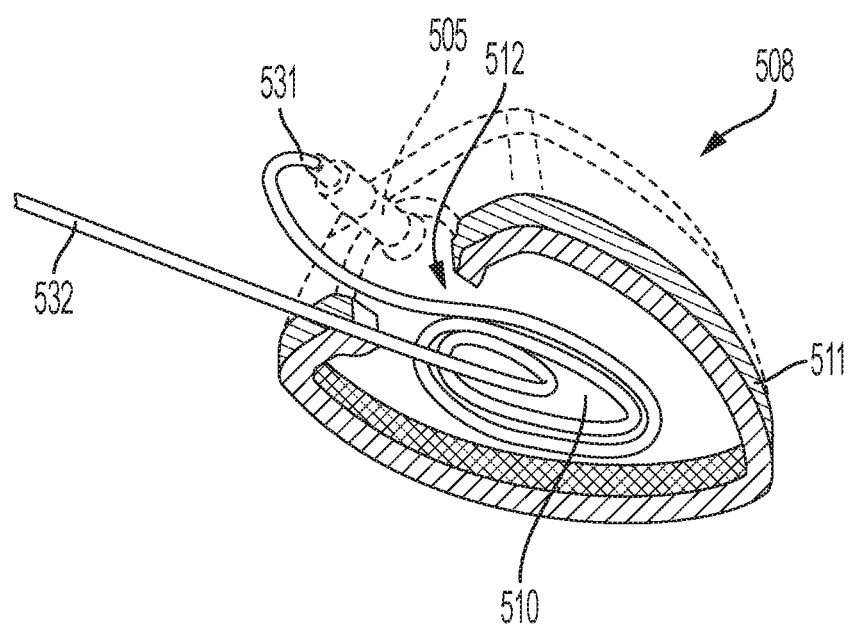
FIG. 5 provides a bottom perspective view of an access port system with three loops of catheter in the catheter compartment.

As illustrated in FIG. 5, once the proximal end of the catheter 531 is secured to the connection ring 505 of the implantable access port system 508, a portion of the proximal end of the catheter 531 is looped one, two, three or more times and inserted into the opening 512 to the catheter compartment 510, with the distal end of the catheter 532 extending from the catheter chamber to the patient's blood vessel, intrathecal space, other lumen or target tissue. When there is an increase in tension on the distal end of the catheter 532 (due to, e.g., growth of a pediatric patient, inflammation, patient movement), the catheter is lengthened with the additional catheter available in the compartment. In an alternate embodiment, the loop closest to the distal end constitutes a half-sized loop. See FIG. 5. As such, the catheter can be lengthened by having some of the additional catheter exit the compartment or can be shortened by having some of the external catheter enter the catheter compartment 510.

In yet another alternate embodiment, the access port is modified to have the exit cannula and connection ring exit directly into a catheter compartment. A winder or retractor mechanism, such as a spring-loaded winder, is added to the catheter compartment, which can take in or release a length of catheter in response to a change in tension of the distal catheter.

The catheter compartment can be located under the housing or along the wall of the access port device. The catheter compartment can be manufactured as an extension of the access port housing using, for example, injection molding or 3D printing technology. In an alternate embodiment, the catheter compartment is produced separately and secured to the bottom or wall of the access port housing using, for example, an adhesive, screws, or sutures. In yet another embodiment, the catheter compartment is positioned under the bottom of the access port housing and secured in place by a sleeve or sock molding made of a stretchable, elastic biocompatible material such as rubber, latex, silicone, or elastomer (e.g., ChronoPrene™ and other thermoplastic elastomers (TPE), thermoset elastomers). The stretchable, elastic biocompatible material is in the shape of a sleeve or a sock that is placed over the access port and catheter compartment with an opening located over the posterior end of the access port system to avoid obstructing the connection ring, the catheter, and the opening of the catheter compartment. The biocompatible sleeve or sock can also have an opening over the septum to provide unimpeded needle penetration. In yet another embodiment, the catheter compartment is an integral component of the stretchable, elastic biocompatible sleeve or sock. The biocompatible sleeve or sock can further comprise a flange or skirt (as shown in 423 of FIG. 4C-D), which provides additional areas for securing or stitching the access port system to the patient's subcutaneous tissue. In yet another embodiment, the biocompatible sleeve is molded with a built-in catheter compartment.

Figure 6A:
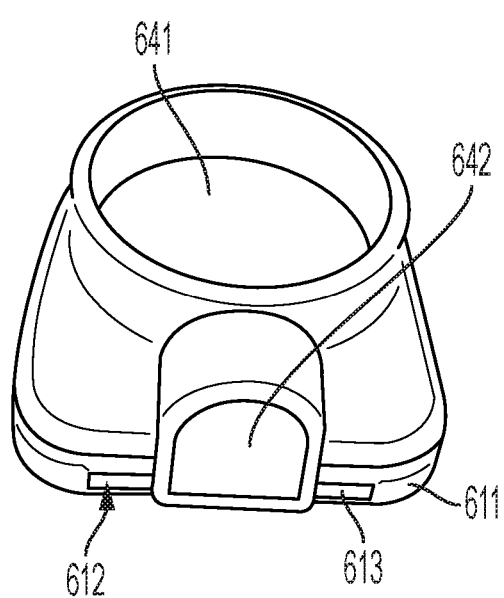
FIG. 6 provides a top perspective view (FIG. 6A) and a rear side perspective view (FIG. 6B) of a stretchable, elastic biocompatible sleeve with a catheter compartment.
Figure 6B:
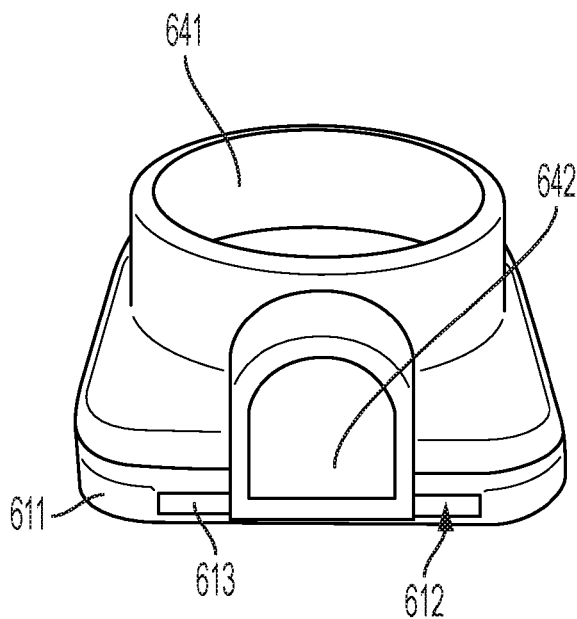

In yet another embodiment, a biocompatible sleeve is custom-molded to cover a commercially-available access port device. The biocompatible sleeve can have an opening located over the posterior end of the access port device (642 in FIG. 6A-B) to avoid obstructing the connection ring, the catheter, and the opening of the catheter compartment. The biocompatible sleeve can also have an opening over the septum (641 in FIG. 6A-B) to provide unimpeded needle penetration. Once the conventional access port device is inserted in the custom-molded biocompatible sleeve (FIGS. 7 A-B), the catheter is secured to the access port device with the connection ring 805 (FIG. 8A), and one or more loops 835 are formed from the proximal end of the catheter 831 and inserted in the catheter compartment 810 of the biocompatible sleeve, as shown in FIG. 8B-D, with the distal end of the catheter 832 extending to the patient's blood vessel, intrathecal space, other lumen or target tissue.

In one embodiment, the custom-molded biocompatible sleeve provides a catheter compartment comprising a peripheral wall 611, a base 613, and an opening 612 under the connection ring opening 642, as shown in FIG. 6.

In an alternative embodiment shown in FIG. 9, the catheter compartment 910 of the custom-molded biocompatible sleeve does not have a base. It only has a peripheral wall 911 extending along almost the entire circumference of the lower part of the biocompatible sleeve with an opening 912 under the connection ring opening 942. Once an access port system is inserted in this biocompatible sleeve through the opening over the septum 941, the access port device/biocompatible sleeve combination is implanted subcutaneously with the peripheral wall 911 resting on and secured to the patient's subcutaneous tissue. The catheter compartment is thus formed by the bottom portion of the biocompatible sleeve (labelled as 910 in FIG. 9A-B), the peripheral wall 911, with the patient's subcutaneous tissue forming the base. In this embodiment, the one or more loops of the catheter can only be inserted in the catheter compartment 910 through the opening 912 after the access port device has been secured to the patient's subcutaneous tissue.

In yet other alternative embodiments, the custom-molded biocompatible sleeve shown in FIGS. 6-9 have a biocompatible flange or skirt extending radially from the peripheral wall of the housing (see 423 in FIG. 4C-D), which is composed of a stretchable, elastic biocompatible material such as rubber, latex, silicone, elastomer (e.g., Chrono-Prene™ and other thermoplastic elastomers (TPE), thermoset elastomers), or other suitable biocompatible material. As described above, the flange or skirt provides a much greater surface area for securing or stitching the access port system to the patient's subcutaneous tissue. It does not have to run along the edge of the entire circumference of the access port device. In an alternative embodiment, the access port device can have 1, 2, 3 or more partial flange or skirts around the circumference of the device.

It should be noted that simply inserting one or more loop under a commercially-available access port device (i.e., a device without a catheter chamber) prior to suturing the device would fail to reduce the risk of catheter-related complication for two reasons. First, without the catheter chamber, movement of the catheter would be constricted as it would be trapped between the access port device and the patient's subcutaneous tissue. Second, without the catheter chamber, the catheter would risk being pierced during the suturing, as the thin catheter can easily be puncture by the sharp surgical needle. The catheter chamber of the present invention protects the catheter during the suturing of the access port device to the patient's subcutaneous tissue and permits easy movement in and out of the catheter upon a change of tension in the distal catheter.

Some embodiments of the technology described herein can be defined according to any of the following numbered paragraphs:

1. An access port device comprising a catheter compartment, wherein a catheter, secured to the access port device, has a portion of a proximal portion of the catheter contained within the catheter compartment and is extensible outside the catheter compartment to increase a length of a distal portion of the catheter or is retractable inside the compartment to decrease the length of the distal portion of the catheter.
2. The access port device of claim 1, wherein the catheter compartment is an extension of the access port device and comprises a peripheral wall running along a portion of an exterior edge of a bottom of the access port device.
3. The access port device of claim 2, wherein the catheter compartment further comprises a base.
4. The access port device of claim 1, wherein the catheter compartment is separate from the access port device and is secured to the access port device.
5. The access port device of claim 4, wherein the catheter compartment is secured to the access port device with a stretchable biocompatible material in a shape of a sleeve or sock.
6. The access port device of any one of claims 1-5, further comprising a biocompatible flange or skirt extending radially from the access port device to provide a surface area for suturing the access port system to a patient.
7. An access port device comprising:
   (a) a housing;
   (b) a septum;
   (c) a fluid reservoir;
   (d) a connection ring; and
   (e) a catheter compartment,
   wherein a catheter, secured to the connection ring, has a portion of a proximal portion of the catheter contained within the catheter compartment and is extensible outside the catheter compartment to increase a length of a distal portion of the catheter or is retractable inside the compartment to decrease the length of the distal portion of the catheter.
8. The access port device of claim 7, wherein the catheter compartment is an extension of the housing and comprises a peripheral wall running along a portion of an exterior edge of a bottom of the access port housing with an opening located under the connection ring.
9. The access port device of claim 8, wherein the catheter compartment further comprises a base.
10. The access port device of claim 7, wherein the catheter compartment is separate from and secured to the access port device.
11. The access port device of claim 10, wherein the catheter compartment is secured to the access port device with a stretchable biocompatible material in a shape of a sleeve or sock, the sleeve or sock having an opening located over a posterior end of the access port device to avoid obstructing the connection ring and the catheter.
12. The access port device of claim 7, wherein the catheter compartment is part of a stretchable, elastic biocompatible sleeve that envelopes the housing of the access port device and has an opening located over a posterior end of the access port device to avoid obstructing the connection ring and the catheter.
13. The access port device of claim 12, wherein the biocompatible sleeve further comprises an opening located over the septum to provide unimpeded needle penetration in the septum.
14. The access port device of any one of claims 7-13, wherein the access port further comprises a biocompatible flange or skirt extending radially from the housing, which provides a greater surface area for suturing the access port device to a patient.
15. A biocompatible sleeve for an access port device comprising:
    (a) a catheter compartment comprising a lateral wall with an opening; and
    (b) an opening for a connection ring of the access port device;
    wherein the biocompatible sleeve envelopes the access port device and a catheter, secured to the connection ring of the access port device, has a portion of a proximal portion contained within the catheter compartment and is extensible outside the catheter compartment to increase a length of a distal portion of the catheter or is retractable inside the catheter compartment to decrease the length of the distal portion of the catheter.
16. The biocompatible sleeve of claim 15, further comprising an opening for a septum of the access port device.
17. The biocompatible sleeve of claim 15, wherein the catheter compartment further comprises a base.
18. The access port system of any one of claims 15-17, wherein the biocompatible sleeve further comprises a biocompatible flange or skirt extending radially from the lateral wall, which provides a greater surface area for suturing the access port device to a patient.
19. The access port system of any one of claims 15-17, wherein the biocompatible sleeve further comprises two or more partial biocompatible flange or skirt extending radially from a portion of the housing, which provides a greater surface area for suturing the access port device to a patient.
20. A method of reducing the rate of access port device failure, the method comprising adding a catheter compartment to an access port device having a catheter, wherein a portion of a proximal portion of the catheter is contained within the catheter compartment and is extensible outside the catheter compartment to increase a length of a distal portion of the catheter, or is retractable inside the catheter compartment to decrease a length of a distal portion of the catheter.

21. The method of claim 20, wherein the addition of the catheter compartment is an extension of the access port device.

22. The method of claim 20, wherein the addition of the catheter compartment is achieved by enveloping a conventional access port device with a biocompatible sleeve with a catheter compartment.

23. The method of any one of claims 20-22, wherein the access port device failure is selected from the group consisting of: catheter dislodgement, catheter migration, port separation with extravasation, and suture disruption.

24. An access port device comprising at least one biocompatible flange or skirt extending radially from the access port device to provide a surface area for suturing the access port device to a patient.

25. The access port device of claim 24, wherein the at least one biocompatible flange or skirt is an extension of the access port device.

26. The access port device of claim 24, wherein the at least one biocompatible flange or skirt is an extension of a custom-designed biocompatible sleeve enveloping the access port device.

27. A method of facilitating the suturing of an access port device to a patient subcutaneous tissue, the method comprising of adding at least one biocompatible flange or skirt extending radially from the access port device to provide a surface area for suturing the access port device to the patient subcutaneous tissue.

28. The method of claim 27, wherein the at least one biocompatible flange or skirt is an extension of the access port device.

29. The method of claim 27, wherein the at least one biocompatible flange or skirt is an extension of a custom-designed biocompatible sleeve enveloping the access port device.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The invention now being generally described, it will be more readily understood by reference to the following examples which are included merely for purposes of illustration of certain aspects and embodiments of the present invention and are not intended to limit the invention.

Example 1

Custom-Molded Biocompatible Sleeve with a Catheter Compartment Having a Lateral Wall and a Base A prototype of a stretchable, elastic biocompatible sleeve with a catheter compartment was custom-designed to tightly envelope a commercially-available, conventional access port device and provide a catheter compartment having a lateral wall and a base. As shown in FIG. 6, the sleeve had an opening 641 on top to avoid obstructing the septum to provide unimpeded needle penetration, an opening 642 located over the posterior end to avoid obstructing the connection ring. The catheter compartment had a base 613 and a lateral wall 611 extending along almost the entire circumference of the lower part of the biocompatible sleeve with an opening 612 under the connection ring opening 642.

Figure 7A:
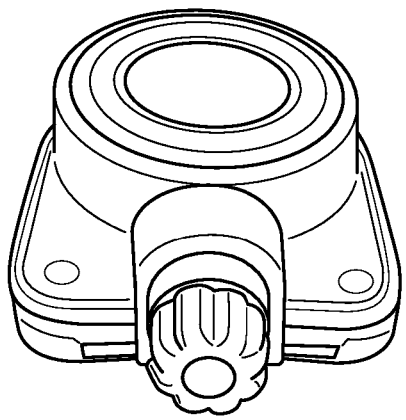
FIG. 7 provides a side perspective view of the rear (FIG. 7A) and the side (FIG. 7B) of a conventional access port device covered by a stretchable, elastic biocompatible sleeve with a catheter compartment comprising a lateral wall, a base, and an opening under the connection ring of the conventional access port system.
Figure 7B:
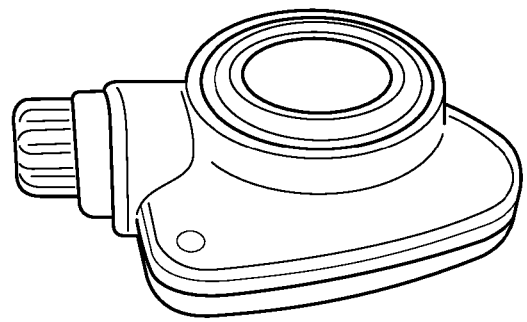
Figure 8A:
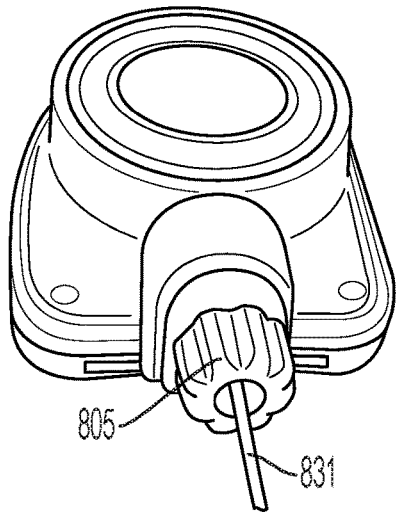
FIG. 8 provides various views of a conventional access port system covered by a stretchable, elastic biocompatible sleeve with a catheter compartment with a catheter secured to the connection ring of the conventional access port system (FIG. 8A), and with a portion of the proximal end of the catheter looped inside the catheter compartment (FIG. 8B-D).
Figure 8B:
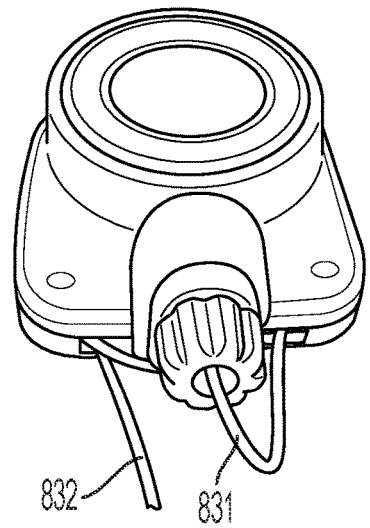
Figure 8C:
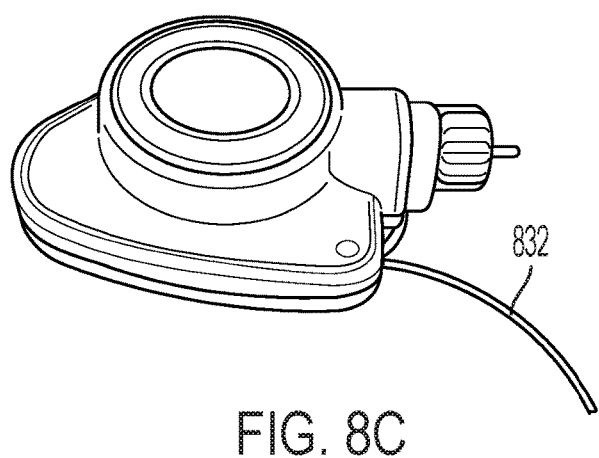
Figure 8D:
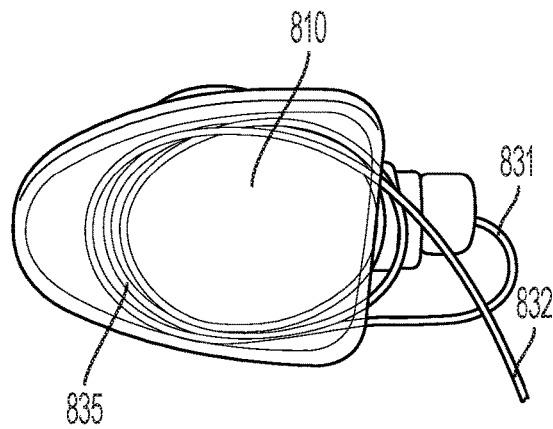
Figure 9A:
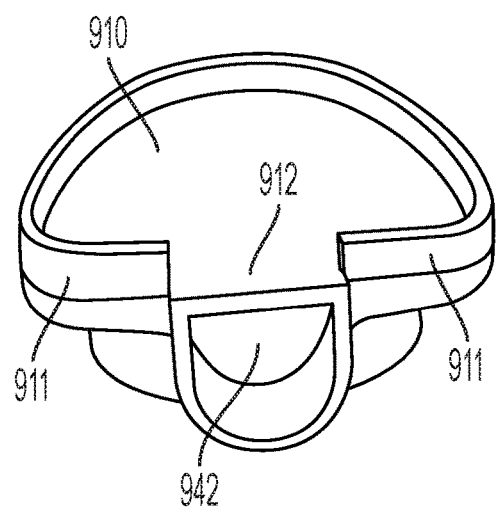
FIG. 9 provides bottom views (FIG. 9A-B) and top views (FIG. 9C-D) of a biocompatible sleeve with a catheter compartment consisting of only a peripheral wall without a base.
Figure 9B:
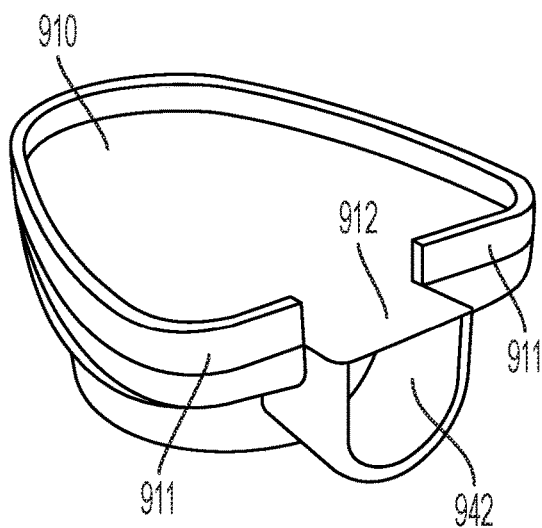
Figure 9C:
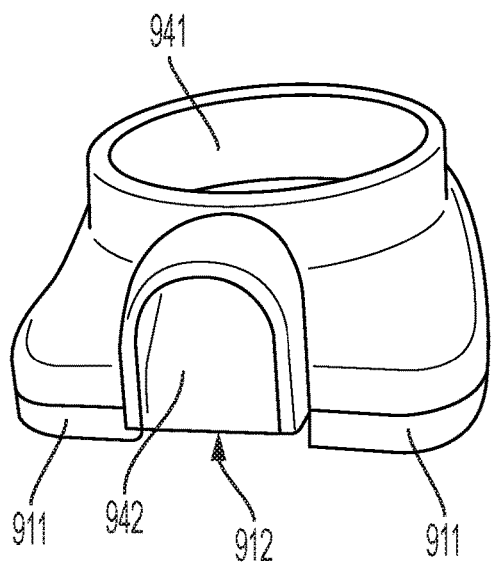
Figure 9D:
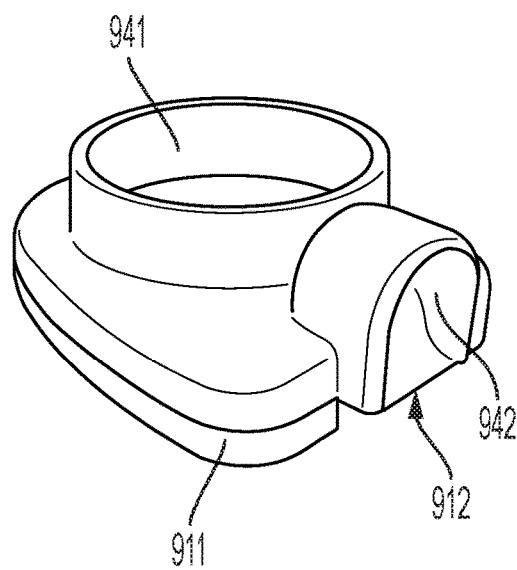

The access port device was inserted in the custom-designed biocompatible sleeve, as shown in FIG. 7. A catheter 831 was then secured to the access port with the connection ring 805 (see FIG. 8A). A portion of the proximal end of the catheter 831 was then looped three times 835 inserted into the catheter compartment 810. FIG. 8B-D show a top, side, and bottom view, respectively, of the conventional access port system enveloped by the stretchable, elastic biocompatible sleeve with three loops of the proximal catheter inside of the catheter compartment.

With a portion of the proximal end of the catheter looped inside the catheter chamber, the catheter could easily be lengthened by pulling the distal portion of the catheter away from the access port system. Conversely, the catheter could easily be shortened by pushing the distal portion of the catheter towards the access port device.

The ability to have the length of the catheter be lengthened or shortened in response to the changes in tension from the distal end of the catheter will help to reduce the rate of access port failures due to dislodgement of catheters, migration of catheters, port separation with extravasation, suture disruption, and catheter migration.

Example 2

Custom-Molded Biocompatible Sleeve with a Catheter Compartment Having a Lateral Wall But Not a Base A second prototype of a stretchable, elastic biocompatible sleeve with a catheter compartment was custom-designed to tightly envelope a commercially-available, conventional access port device and provide a catheter compartment having a lateral wall without a base. As shown in FIG. 9, this second sleeve also had an opening 941 (FIG. 9C-D) to avoid obstructing the septum to provide unimpeded needle penetration and an opening 942 located over the posterior end to avoid obstructing the connection ring (FIG. 9A-D). The catheter compartment had a lateral wall 911 extending along almost the entire circumference of the lower part of the biocompatible sleeve with an opening 912 under the connection ring opening 942 but it did not have a base.

The access port device was inserted in the custom-designed biocompatible sleeve (not shown). A catheter was then secured to the access port with the connection ring. The device was secured to a hard surface and a portion of the proximal end of the catheter was looped three times and inserted into the catheter compartment.

With a portion of the proximal end of the catheter looped inside the catheter chamber, the catheter could easily be lengthened by pulling the distal portion of the catheter away from the access port system. Conversely, the catheter could easily be shortened by pushing the distal portion of the catheter towards the access port device.

The ability to have the length of the catheter be lengthened or shortened in response to the changes in tension from the distal end of the catheter will help to reduce the rate of access port failures due to dislodgement of catheters, migration of catheters, port separation with extravasation, suture disruption, and catheter migration.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The foregoing written specification is considered to be sufficient to enable one skilled in the art to practice the present aspects and embodiments. The present aspects and embodiments are not to be limited in scope by examples provided, since the examples are intended as a single illustration of one aspect and other functionally equivalent embodiments are within the scope of the disclosure. Various modifications in addition to those shown and described herein will become apparent to those skilled in the art from the foregoing description and fall within the scope of the appended claims. The advantages and objects described herein are not necessarily encompassed by each embodiment. Those skilled in the art will recognize or be able to ascertain using no more than routine experimentation, many equivalents to the specific embodiments described herein. Such equivalents are intended to be encompassed by the following claims.

REFERENCES

[1] See, e.g., U.S. Pat. Nos. 9,764,124; 9,358,378; 9,174,037; 8,876,788; 8,100,866; and 7,114,701 and published US Patent Application Nos. 2016/0325084; 2017/0000995; 2017/0014611; and 2017/0028185.

[2] Samad, A. M. A. and Ibrahim, Y. A. (2015). *Complications of Port A Cath implantation: A single institution experience.* The Egyptian Journal of Radiology and Nuclear Medicine, 46(4): 907-911.

Wang, S.-H. et al. (2013). *Dislodgement of port-A catheters in pediatric oncology patients:* 11 *years of experience.* World Journal of Surgical Oncology, 11: 191.

Ho, C.-L., et al. (2008). *Dislodgment of Port-A-Cath Catheters in Children.* Pediatric Neonatology, 49(5): 179-182.

Dillon, P. A. and Foglia, R. P. (2006). *Complications associated with an implantable vascular access device.* Journal of Pediatric Surgery, 41: 1582-1587.

Tsai, T.-N. et al. (2006). *Transcatheter retrieval of dislodged Port-A catheter fragments: experience with 47 cases.* Acta Cardiologica Sinica, 22: 221-228.

Yen, H. J. et al. (2006). *Transcatheter retrieval of different types of central venous catheter fragment: experience in 13 cases.* Angiology, 57: 347-353.

Liu, J. C. et al. (2004). *Percutaneous retrieval of 20 centrally dislodged Port-A catheter fragments.* Clinical Imaging, 28: 223-229.

Fazeny-Darner, B. et al. (2003). *Central venous catheter pinch-off and fracture: recognition, prevention and management.* Bone Marrow Transplant, 31: 927-930.

Babu, R. and Spicer, R. D. (2002). *Implanted vascular access devices (ports) in children: complications and their prevention.* Pediatric Surgery International, 18: 50-53.

Wu, J. R. et al. (2002). *Nonsurgical percutaneous retrieval of dislodged Port-A catheters from pulmonary artery in children.* Japanese Heart Journal, 43: 295-300.

Biffi, R. et al. (1998). *Totally implantable central venous access ports for long-term chemotherapy: a prospective study analyzing complications and costs of 333 devices with a minimum follow-up of 180 days.* Annals of Oncology, 9: 767-773.

Fuenfer, M. M. et al. (1998). *Etiology and retrieval of retained central venous catheter fragments within the heart and great vessels of infants and children.* Journal of Pediatric Surgery, 33: 454-456.

Kock, H. J. et al. (1998). *Implantable vascular access systems: experience in 1500 patients with totally implanted central venous port systems.* World Journal of Surgery, 22: 12-16.

Yedlicka, J. W. et al. (1991). *Nitinol gooseneck snare for removal of foreign bodies: experimental study and clinical evaluation.* Radiology, 178: 691-693.

Massumi, R. A. and Ross, A. M. (1967). *A traumatic, nonsurgical technic for removal of broken catheters from cardiac cavities.* New England Journal of Medicine, 277: 195-196.

Thomas, J. et al. (1964). *Non-surgical retrieval of a broken segment of steel spring guide from the right atrium and inferior vena cava.* Circulation, 30: 106-108.

[3] Babu, R. and Spicer, R. D. (2002). *Implanted vascular access devices (ports) in children: complications and their prevention.* Pediatric Surgery International, 18: 50-53.

Dillon, P. A. and Foglia, R. P. (2006). *Complications associated with an implantable vascular access device.* Journal of Pediatric Surgery, 41: 1582-1587.

[4] Anitescu, M. et al. (2012). *Intrapleural Migration of a Spinal Catheter in a Patient With Arachnoiditis and*

Extensive Epidural Scarring After Tethered Cord Release: A Case Report and Review of Literature. Neuromodulation, 15(3): 200-203.

Staats, P. S. (2008). *Complications of Intrathecal Therapy*. Pain Medicine, 9 (Suppl 1): S102-S107.

Follett, K. A., et al. (2003). *Prevention of Intrathecal Drug Delivery Catheter-Related Complications*. International Neuromodulation Society, 6(1): 32-41.

Follett, K. A. and Naumann, C. P. (2000). *A Prospective Study of Catheter-Related Complications of Intrathecal Drug Delivery Systems*. Journal of Pain and Symptom Management, 19(3): 209-215.

[5] Hitt, J. M. and de Leon-Casasola, O. A. (2011). *Complications of intrathecal drug delivery systems*. Techniques in Regional Anesthesia and Pain Management, 15(4): 162-166.

Follet, K. A. et al. (2003). *Prevention of intrathecal drug delivery catheter-related complications*. Neuromodulation, 6: 32-41.

Kamran, S. and Wright, B. D. (2001). *Complications of intrathecal drug delivery systems*. Neuromodulation, 4(3): 111-115.

Follett, K. A. and Naumann, C. P. (2000). *A prospective study of catheter-related complications of intrathecal drug delivery systems*. Journal of Pain Symptom Management, 19: 209 215.

Penn, R. D. (1996). *Catheter implant systems for intrathecal drug delivery*. Journal of Neurosurgery, 84: 713.

Tutak, U. and Doleys, D. M. (1996). *Intrathecal infusion systems for treatment of chronic low back and leg pain of non-cancer origin*. The Southern Medical Journal, 89: 295-300.

Winkelmüller, M. and Winkelmüller, P. (1996). *Long-term effect of continuous opioid treatment in chronic pain of non-malignant etiology*. Journal of Neurosurgery, 85(3): 458-467.

Paice, J. A. et al. (1991). *Intraspinal morphine for chronic pain: a retrospective, multicenter study*. Journal of Pain Symptom Management, 11:71-80.

Hirsh, L. F. et al. (1985). *Sudden loss of pain control with morphine pump due to catheter migration*. Neurosurgery, 17(6): 965-967.

[6] Follett, K. A. and Naumann, C. P. (2000). *A prospective study of catheter-related complications of intrathecal drug delivery systems*. Journal of Pain Symptom Management, 19: 209-215.

[7] Fluckiger, B., et al. (2008). *Device-related complications of long-term intrathecal drug therapy via implanted pumps*. Spinal Cord, 46: 639-643.

[8] Kock, H. J. et al. (1998). *Implantable vascular access systems: experience in 1500 patients with totally implanted central venous port systems*. World Journal of Surgery, 22: 12-16.

Biffi, R. et al. (1998). *Totally implantable central venous access ports for long-term chemotherapy: a prospective study analyzing complications and costs of 333 devices with a minimum follow-up of 180 days*. Annals of Oncology, 9: 767-773.

[9] Albrecht, E. et al. (2005). *Intraparenchymal migration of an intrathecal catheter three years after implantation*. Pain, 118: 274-278.

We claim:

1. An access port device for implantation in a subject, the access port device comprising a catheter compartment, wherein the catheter compartment is an extension of the access port device and comprises a peripheral wall running along a portion of an exterior edge of a bottom of the access port device, and wherein
   a catheter, secured to the access port device, has a portion of a proximal portion of the catheter contained within the catheter compartment, and
   after the device has been implanted in the subject, the catheter is extensible outside the catheter compartment to increase a length of a distal portion of the catheter in response to an increase in tension on the distal portion or is retractable inside the compartment to decrease the length of the distal portion of the catheter in response to a decrease in tension on the distal portion.

2. The access port device of claim 1, wherein the catheter compartment further comprises a base.

3. The access port device of claim 1, wherein the catheter compartment is separate from the access port device and is secured to the access port device.

4. The access port device of claim 3, wherein the catheter compartment is secured to the access port device with a stretchable biocompatible material in a shape of a sleeve or sock.

5. The access port device of claim 1, further comprising a biocompatible flange or skirt extending radially from the access port device to provide a surface area for suturing the access port system to a patient.

6. An access port device for implantation in a subject, the access port device comprising:
   (a) a housing;
   (b) a septum;
   (c) a fluid reservoir;
   (d) a connection ring; and
   (e) a catheter compartment,
   wherein a catheter, secured to the connection ring, has a portion of a proximal portion of the catheter contained within the catheter compartment, and
   after the device has been implanted in the subject, the catheter is extensible outside the catheter compartment to increase a length of a distal portion of the catheter in response to an increase in tension on the distal portion or is retractable inside the compartment to decrease the length of the distal portion of the catheter in response to a decrease in tension on the distal portion.

7. The access port device of claim 6, wherein the catheter compartment is an extension of the housing and comprises a peripheral wall running along a portion of an exterior edge of a bottom of the housing with an opening located under the connection ring.

8. The access port device of claim 7, wherein the catheter compartment further comprises a base.

9. The access port device of claim 6, wherein the catheter compartment is separate from and secured to the access port device.

10. The access port device of claim 9, wherein the catheter compartment is secured to the access port device with a stretchable biocompatible material in a shape of a sleeve or sock, the sleeve or sock having an opening located over a posterior end of the access port device to avoid obstructing the connection ring and the catheter.

11. The access port device of claim 6, wherein the catheter compartment is part of a stretchable, elastic biocompatible sleeve that envelopes the housing of the access port device and has an opening located over a posterior end of the access port device to avoid obstructing the connection ring and the catheter.

12. The access port device of claim 11, wherein the biocompatible sleeve further comprises an opening located over the septum to provide unimpeded needle penetration in the septum.

13. The access port device of claim 6, wherein the access port device further comprises a biocompatible flange or skirt extending radially from the housing, which provides a greater surface area for suturing the access port device to a patient.

14. The access port system of claim 6, wherein the access port device further comprises two or more partial biocompatible flanges or skirts extending radially from a portion of the housing, which provides a greater surface area for suturing the access port device to a patient.

* * * * *